United States Patent [19]

Marshall et al.

[11] Patent Number: 5,609,605
[45] Date of Patent: Mar. 11, 1997

[54] COMBINATION ARTERIAL STENT

[75] Inventors: Paul Marshall, Washington Crossing; Anthony S. Miksza, Bethlehem, both of Pa.

[73] Assignee: Ethicon, Inc., Somerville, N.J.

[21] Appl. No.: 434,615

[22] Filed: May 4, 1995

Related U.S. Application Data

[62] Division of Ser. No. 296,216, Aug. 25, 1994.

[51] Int. Cl.⁶ .................................................. A61M 29/00
[52] U.S. Cl. ........................ 606/191; 606/194; 606/198; 606/108; 623/1; 623/12
[58] Field of Search ........................ 606/108, 191, 606/198, 194; 623/1, 12; 604/96, 97, 98

[56] References Cited

U.S. PATENT DOCUMENTS

| | | | |
|---|---|---|---|
| 4,763,654 | 8/1988 | Jang | 128/344 |
| 5,002,532 | 3/1991 | Gaiser et al. | 606/194 |
| 5,219,355 | 6/1993 | Parodi et al. | 606/191 |
| 5,360,443 | 11/1994 | Barone et al. | 623/1 |
| 5,383,892 | 1/1995 | Cardon et al. | 606/198 |

*Primary Examiner*—Michael Powell Buiz
*Assistant Examiner*—Kevin Truong
*Attorney, Agent, or Firm*—Paul A. Coletti

[57] ABSTRACT

A stent which may be emplaced into the lumen of the body. The stent has an expandable first section with a first diameter and an expanded second diameter larger than its first diameter. There is also a second section connected to the first section, the second section contains a third diameter and an expanded fourth diameter which is larger than the third diameter. Finally, the second diameter is different from the fourth diameter. Thus, the device may be emplaced between lumens of different sizes. Ideally, this stent can be placed at the junction at the aorta and the iliac arteries, where the size of the lumens are typically different. In use, therefore, the device provides the surgeon with a useful tool to holding open junctions of various sized lumens.

4 Claims, 5 Drawing Sheets

COMBINATION ARTERIAL STENT

This is a division of application Ser. No. 08/296,216, filed Aug. 25, 1994, which is hereby incorporated by reference.

BACKGROUND OF THE INVENTION

Generally this invention relates to stents for emplacement within interior body lumens. More particularly, this relates to a combination stent wherein one stent is of a different size than the other stent.

The use of stents to maintain lumens of the body open in order to allow the passage of fluids therethrough, has become quite common. Particularly useful are coronary stents which allow the coronary arteries to be maintained patent even when there are lesions in these arteries due to diseases such as arteriosclerosis. These stents are also useful for such as the aorta or the iliac artery.

One particular area where stents are seen as useful are at the junction of the iliac arteries into the aorta. However, it can be appreciated that due to the difference in diameter between the iliac arteries and the aorta, it would be a complex problem to create a stent which would hold open both the aorta at the junction of the arteries and one or both of the arteries. This invention addresses such a problem.

SUMMARY OF THE INVENTION

This invention comprises a stent which may be emplaced into the lumen of the body. The stent has an expandable first section with a first diameter and an expanded second diameter larger than its first diameter. There is also a second section connected to the first section, the second section contains a third diameter and an expanded fourth diameter which is larger than the third diameter. A final criterion to this invention is that the second diameter is different from the fourth diameter. Thus, the device may be emplaced between lumens of different sizes.

One particular method of manufacturing this stent is to provided the stent with a first portion which contains a cylindrical shape and a longitudinal axis. The cylindrical shape contains an array of slots arranged around the diameter of the cylinder. The slots have a relaxed dimension and an enlarged dimension around the circumference of the cylinder. The enlarged dimension of each of the slots causes the cylindrical shape to increase in diameter. Also, it causes the slots to decease in lengths so that the cylindrical diameter of the stent in its first portion enlarges during the enlargement of the first portion. There is also contained on such a stent a second portion very similar to the first portion. It too contains an array of slots arranged around the diameter of a second cylinder. It too contains an enlarged dimension and a relaxed dimension. However, importantly, in order to make this invention, the first portion slot lengths are of a different size, typically greater than, the second portion slot lengths. Thus, the user is able once again able to enlarge the first portion to a different size than the second portion.

One of the important ways of causing such an enlargement is too provide a balloon catheter which is ideally formulated to create such a mechanism. The catheter comprises a generally cylindrically expandable length. The length has first sections, each of which have expanded diameters. Again, however, each of the first and second expanded diameters are of different dimensions. Thus, when emplaced on the first and second stent portions, respectively, the user is again able to enlarge the first portion to a different diameter than the second portion.

Ideally, this stent can be placed at the junction at the aorta and the iliac arteries, where the size of the lumens are typically different. In use, therefore, the device provides the surgeon with a useful tool to holding open junctions of various sized lumens.

DESCRIPTION OF THE DRAWINGS

The invention described above will be better understood in conjunction with the following drawings wherein.

DETAILED DESCRIPTION OF THE INVENTION

Figure 1A:
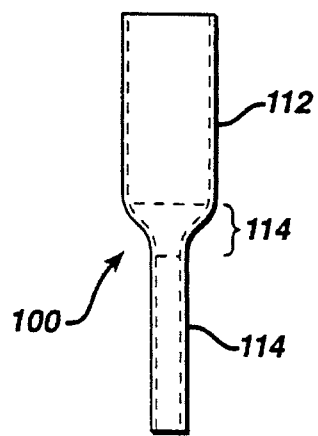
FIGS. 1a, 1b and 1c describe the various methods of manufacture of the stent of the present invention.
Figure 1B:
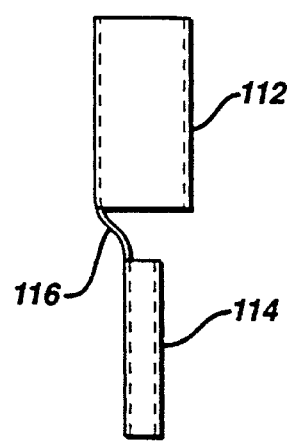
Figure 1C:
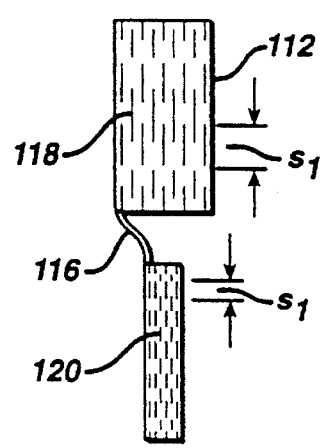
Figure 6:
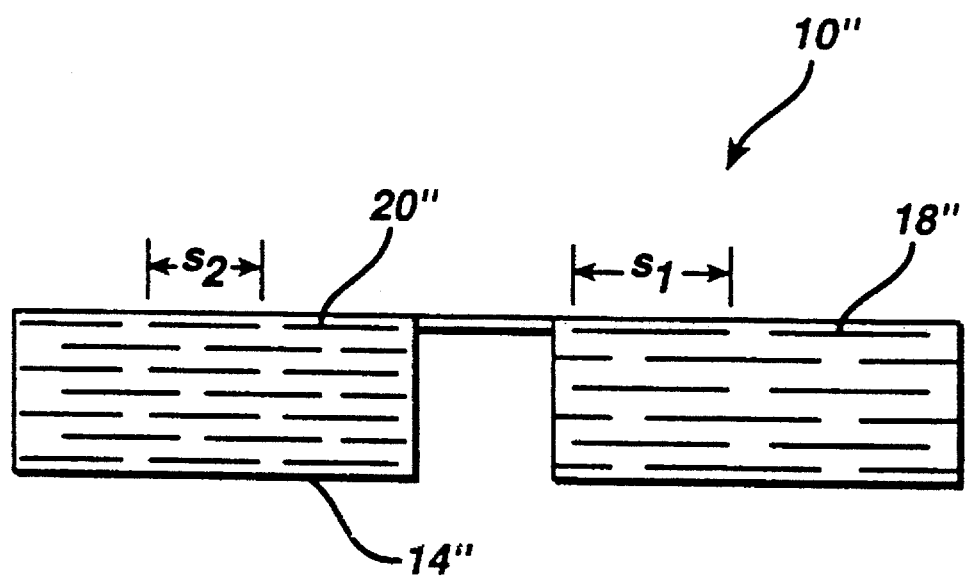
FIG. 6 shows yet another alternate embodiment of the invention.

As seen in the drawings there is contained in this invention an articulated or stepped stent 10 having two sections. The first section 12 has a given length $l_1$ and a given diameter $d_1$. The second section 14 has a given second given length $l_2$ and a second given diameter $d_2$. Each of these sections 12, 14 are connected by a connector 16. The first section 12 similarly contains a series of elongated slots 18 of a first length $s_1$. The second section similarly contains a series of elongated slots 20 of a second length $s_2$. The size of the first length $s_1$ will be different than the size of the second length $s_2$. Similarly, the stent 10" of FIG. 6 contains similar diameter sections 12", 14", but different length slots 18" ($s_1$), 20" ($s_2$); the stent 10" of FIG. 6 produces the same result as the stent of FIGS. 1c and 2, according to this invention.

Figure 4:
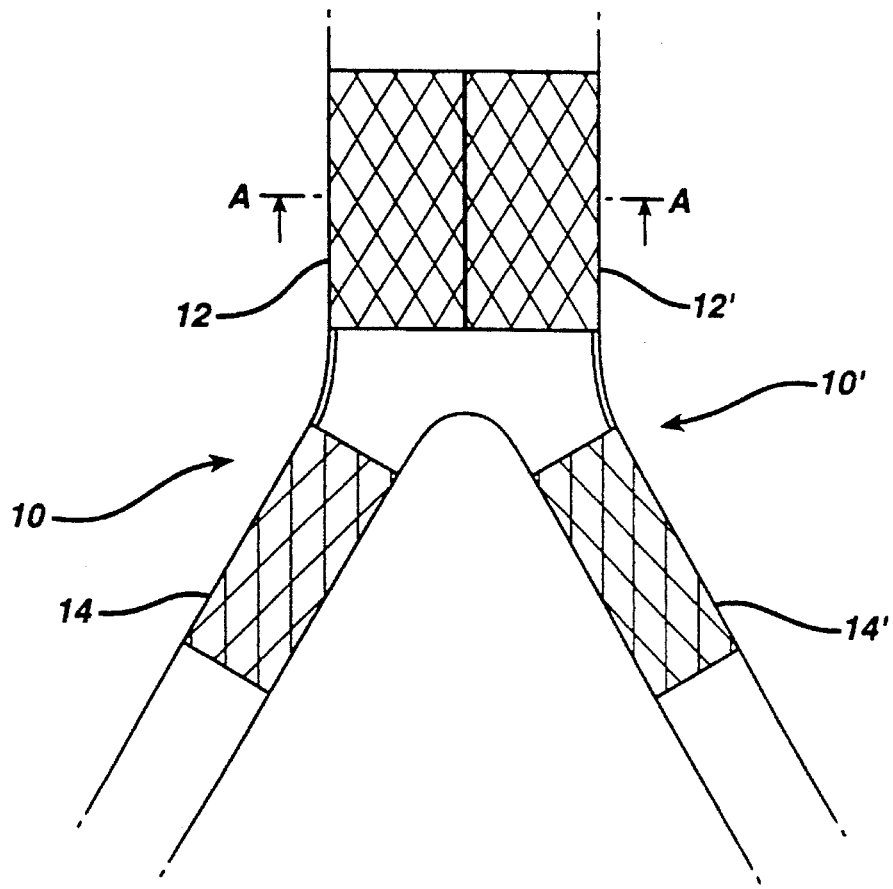
FIG. 4 shows a placement of two stents of the present invention within the body.

In use therefore the stent 10 of the present invention may be placed at the junction of the iliac artery and the aorta as seen in FIG. 4. The size of the first section 12 will be enlarged to accommodate the size of the aorta. The size of the second section 14 will be enlarged to accommodate the size of the iliac artery, different than the size of the aorta. It will be appreciated therefore, that the sizes of the slots 18, 20 when in the enlarged state will expand to different sizes in order to accommodate the lumens to which the sections of the stent are emplaced.

Figure 2:
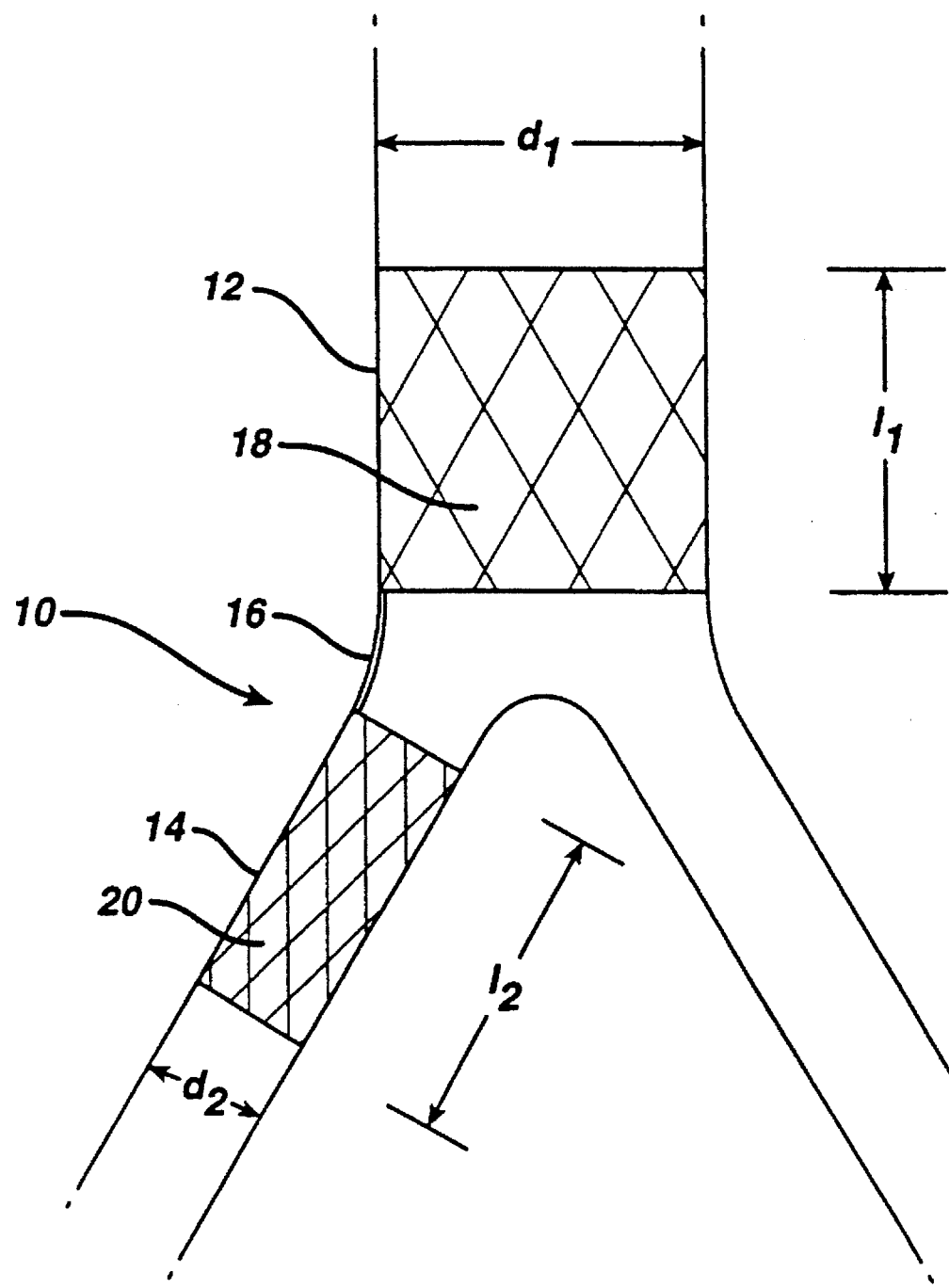
FIG. 2 shows a stent of the present invention placed within the body.

Manufacture of the stent of FIG. 2 is described below. First, a piece of stepped tubing 100 is designed so that there is a neckdown roughly in the place where the first section 112 is attached to the second section 114. Then, a cylindrical portion of tubing 114 is removed, specifically at the area of the neckdown of the stepped tubing forming connector 116. Then, slots 118, 120 are emplaced within the first and second sections 112, 114, wherein the second sections 114 contains smaller slots 120 than in the first section 112. Thus, when enlarged the second section 114 cannot be enlarged to be the size of the first section 112. In other words, both sections 112, 114 have different initial and final sizes.

Figure 3:
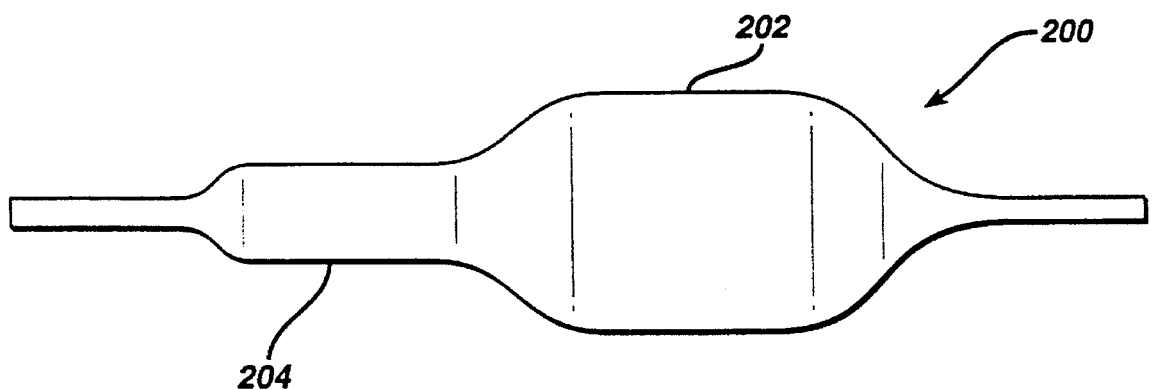
FIG. 3 shows a balloon useful for placing the stent of FIG. 2 within the body.

Similarly, as seen in FIG. 3, a stepped balloon 200 is useful to emplace the stent of this invention. The balloon contains a first section 202 which is useful to be emplaced within the first section 12 of the stent 10 described above. The second section 204 of the balloon 200 is emplaced within the second section 14 of the stent 10 described above. When enlarged, the balloon 200 of present invention enlarges each respective section 12, 14 of the stent 10 to its enlarged size for emplacement within a lumen of the body.

Figure 5:
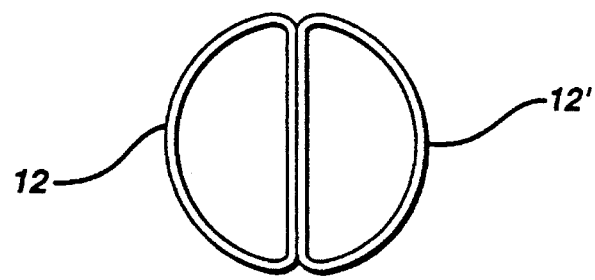
FIG. 5 shows a cross sectional view of FIG. 4 taken across lines A—A of FIG. 4.

Finally as seen in FIGS. 4 and 5 the stents 10, 10' of the present invention may be useful in combination with a complimentary stent to enlarge both iliac arteries and the aorta simultaneously. Here, the size of the first section 12, 12' is roughly one-half the size of the aorta. The size of the second section 14, 14' of the stents 10, 10' are roughly the size of an iliac artery. When placed together, these articulating stents hold open both iliac arteries (by enlargement of both second sections 14, 14' of each of the stents 10, 10') and also holds open the aorta as seen in FIG. 5 (by enlargement each of the first sections 12, 12' of the stents 10, 10' described in FIGS. 4 and 5). Thus, the combination proves quite useful for one with artherosclerosis in many blood vessels, and also for anchoring a prosthetic graft to a stent in such procedures.

It will be appreciated that the above described invention may be useful with various modifications and minor alterations to the design of the present invention. Therefore, the scope of the invention in intended to be encompassed by the appended claims and their equivalents.

We claim:

1. A medical device comprising a balloon in combination with at least two stents, said balloon comprising a generally cylindrically expandable length, said length having first and second sections each of which have expanded diameters, and said first and second section expanded diameters having different dimensions; and each of said at least two stents carried on a separate section of said balloon.

2. The medical device of claim 1 wherein said balloon is disposed on the distal end of an inflating catheter.

3. The medical device of claim 1 wherein said balloon sections have similar unexpanded diameters.

4. The medical device of claim 1 wherein said first section is distal said second section, and said first section has a larger expanded diameter than said second section.

* * * * *